United States Patent [19]
> Bledsoe

[11] 4,407,276
[45] Oct. 4, 1983

[54] BRACE FOR ARTICULATED LIMBS

[75] Inventor: Gary R. Bledsoe, Arlington, Tex.

[73] Assignee: Medical Designs, Inc., Arlington, Tex.

[21] Appl. No.: 227,381

[22] Filed: Jan. 22, 1981

[51] Int. Cl.³ .......................... A61F 3/00; A61F 5/00
[52] U.S. Cl. ............................... 128/80 C; 128/80 R; 128/80 H; 128/DIG. 15
[58] Field of Search ........... 128/80 C, 87 R, DIG. 15, 128/80 F, 80 H

[56] References Cited

U.S. PATENT DOCUMENTS

| | | | |
|---|---|---|---|
| 1,510,408 | 9/1924 | Lychou | 128/80 C |
| 2,632,440 | 3/1953 | Hauser et al. | 128/80 |
| 3,232,289 | 2/1966 | Zimmerman | 128/DIG. 15 |
| 3,535,718 | 10/1970 | Morcott | 128/DIG. 15 |
| 3,575,166 | 4/1971 | Rosman | 128/80 |
| 3,581,741 | 6/1971 | Rosman | 128/80 |
| 3,669,105 | 6/1972 | Castiglia | 128/80 C |
| 3,785,372 | 1/1974 | Craig | 128/84 R |
| 3,786,804 | 1/1974 | Lewis | 128/80 C |
| 3,826,251 | 7/1974 | Ross | 128/80 F |
| 3,827,431 | 8/1974 | Pecorella | 128/80 F |
| 3,844,279 | 10/1974 | Konvalin | 128/80 F |
| 3,853,123 | 12/1974 | Moore | 128/80 C |
| 3,935,858 | 2/1976 | Harroff | 128/80 C |
| 4,013,070 | 3/1977 | Harroff | 128/80 C |
| 4,019,504 | 4/1977 | Sterling | 128/DIG. 15 |
| 4,041,940 | 8/1977 | Frankel et al. | 128/80 C |
| 4,084,584 | 4/1978 | Detty | 128/80 C |
| 4,090,508 | 5/1978 | Gaylord, Jr. | 128/80 C |
| 4,111,194 | 9/1978 | Cox et al. | 128/80 C |
| 4,136,404 | 1/1979 | Lange | 128/80 R |
| 4,220,148 | 9/1980 | Lehneis | 128/80 C |
| 4,233,967 | 11/1980 | Daniell, Jr. | 128/80 C |
| 4,241,730 | 12/1980 | Helfet | 128/80 C |
| 4,270,527 | 6/1981 | Peters et al. | 128/87 R |
| 4,271,831 | 6/1981 | Deibert | 128/80 C |
| 4,296,744 | 10/1981 | Palumbo | 128/80 C |

*Primary Examiner*—Kyle L. Howell
*Assistant Examiner*—C. W. Shedd

*Attorney, Agent, or Firm*—Charles W. McHugh

[57] ABSTRACT

A light-weight brace adapted to be affixed externally of a patient's leg so that it lies partly above and partly below the person's knee. The apparatus includes first and second flexible sheets of cushioned material which are adapted to be snugly wrapped around the thigh and calf. The width of each of the flexible sheets is sufficient to circumferentially envelope at least most, and preferably all, of its associated leg member; and the length of each sheet is sufficient to encompass at least half of the length of the respective leg member. A preferred cushioning material is a sheet of polyurethane foam (about 9 mm thick) bonded to a sheet of pile-type material having sufficient "nap" to serve as an anchor for resilient hooks of the Velcro type. Also provided are first and second pairs of elongated braces, which braces are relatively stiff so as to resist both torsion and bending loads. The pairs of elongated braces are adapted to lie on opposite sides of the wearer's thigh and calf. The elongated braces consist of structural cores which are preferably enclosed in non-metallic sheaths of vinyl or the like; the cores are bonded to said sheaths in order to inhibit any relative motion between the exterior sheaths and the interior cores. Permanently attached to the outer surface of the sheaths are pads of resilient hook material, such that the elongated braces may be selectively positioned next to and engaged with the pile side of the flexible sheets. Exact positioning of the elongated braces is a matter of choice, and a hinge which connects respective ones of the elongated braces is positioned in accordance with well-known medical principles. A plurality of non-elastic straps are provided for wrapping circumferentially around the respective leg members so as to tightly hold the respective sheet members about the thigh and calf. Additional Velcro-type fastening elements are mounted on the interior surface of the non-elastic straps and the exterior surface of the elongated braces, such that the braces may be more effectively anchored to the leg.

8 Claims, 7 Drawing Figures

BRACE FOR ARTICULATED LIMBS

This invention relates generally to devices for controlling the degree of motion which is permitted between the proximal and distal members of a person's lower limbs; more particularly, it relates to an external brace having hinge devices adjacent a knee which may be adjusted to selectively control the amount of motion which is permitted between the two members. Additionally, the invention relates to removable and replaceable braces which are adapted to take the place of conventional rigid casts.

It is well known to externally support a person's limbs to foster healing, such as when an injury has occurred to the ligaments in a joint in a person's limbs, etc. Orthopedic specialists routinely treat a person's bones, joints and connective tissues by use of external castings, splints, wraps and braces—until the body's natural healing processes have been completed. When the injury involves a person's legs, extra problems arise because of the supportive function which the legs must provide, as well as the very special construction of the knee. And anyone who has ever experienced a "bad knee" can testify that a person's legs constitutes particularly important parts of a body, because they furnish the mobility which is required in order to perform routine daily functions. Therefore, most surgeons—and patients—feel that leg injuries should be handled as a matter of very high priority The old practice of treating a knee injury by placing most of the leg in a rigid cast and leaving the cast in place for weeks (or even months) is now being discarded by many surgeons in favor of short-term casting. When possible, a patient is left in a rigid cast for the shortest feasible period of time, and then the knee is supported for a longer period of time with a brace of some kind. Ideally, the brace allows at least some degree of exercise for the patient's muscles, so that they do not become unreasonably weak through lack of use. Cast bracing has not been without its problems, however, including the fact that the application of a cast is usually time-consuming and often messy—even when using new synthetic casting material instead of well-known plaster of Paris. Conventional casts are typically very bulky, and they have often been condemned by patients as being uncomfortable—especially after they have been in place for more than a few days. Patients are denied the opportunity to bathe while wearing a cast, and skin maceration is often a problem; complications involving a patient's skin are particularly troublesome with those patients who sweat excessively. Hence, there has long remained a need for an improved device which can support a person's limbs in accordance with medical needs while minimizing the practical problems that have been enumerated.

Another problem with prior art devices has been the difficulty of providing a variation in permissible motion in a person's limbs as an injured joint (the knee) or tissue is healing. Immediately following surgery, a surgeon may wish to completely inhibit motion between the major bones (i.e., the tibia and femur) in a patient's limbs. Later, after at least some healing has taken place, the surgeon may wish to permit a certain amount of movement. Or, the nature of the injury may not even require surgery—but the surgeon wishes to restrict certain types of leg motion until some damaged tissue has healed itself. Some surgeons may favor applying a knee brace to permit, say, 30° of movement between the major bones of a leg (e.g., between an initial angle of 30° to a subsequent angle of 60°), while others may favor as much as 50° of relative movement (e.g., 20° to 70°). Hence, there has been a need for a brace which could be accurately categorized as being essentially "universal", in that it is capable of being used to immobilize a person's limbs in either a straight position or some bent position (e.g., 70°), as well as permitting a wide range of motions extending from, say, 30° to 135°, in a variety of increments.

Of course, there have been other devices which have been proposed from time to time to accomplish some of the above-described tasks. Exemplary of previously taught devices include those shown in U.S. Pat. Nos. 3,669,105 entitled "Brace for Articulated Limbs"; 3,762,405 entitled "Traction Splint Assembly"; 4,201,203 entitled "Knee Brace"; 4,214,577 entitled "Orthosis for Exercising Joint"; 4,220,148 entitled "Knee Stabilizer"; and 4,233,967 entitled "Custom-Fitted Knee Guard and Brace". Additionally, it is known that there are some commercially available products called "universal knee splints" or "knee immobilizers" which are marketed by numerous medical device manufacturers, including Orthopedic Equipment Co., Inc., Zimmer Manufacturing Company, and Medical Specialties, Inc. While all of these various devices of the prior art may have solved one or more special problems, none of them have offered the versatility that often has been desired by doctors (to foster healing) and patients (to provide comfort). Hence, there has remained a need for an improved brace which provides the best features of previously known devices and also introduces new capabilities which were not previously possible. Accordingly, it is an object of this invention to provide a greatly improved brace for controlling the motion about the knee in a person's legs.

Another object is to provide a leg brace which is capable of being quickly and easily applied, and which requires no messy compounds or uncomfortable curing media (such as heat).

Still another object is to provide a brace which can be removed at will, so that a doctor might examine the progress of healing, but which can be readily replaced on a patient's leg without losing any of its original effectiveness.

One more object is to provide a brace for a person's limbs which is readily adjustable in size at any desired time, so as to compensate for increases or decreases in tissue sizes as a result of either swelling or muscle atrophy.

A further object is to provide a knee brace which has sufficient durability to be functional throughout the entire healing process for most typical knee injuries, but which is not so expensive that it cannot be realistically discarded after it has been satisfactorily used by a single patient.

These and other objects will be apparent from a reading of the specification and the claims appended thereto, and the attached drawing in which FIG. 1 is an elevational view of an embodiment of the invention adapted for controlling relative movement between the major elements of a person's leg, with the device being completely assembled as if it was mounted on a leg—and showing the right side thereof;

FIG. 2 is a rear elevational view of the knee brace shown in FIG. 1;

FIG. 3 is an elevational view of the knee brace as seen from the left side of the brace;

Figure 4:
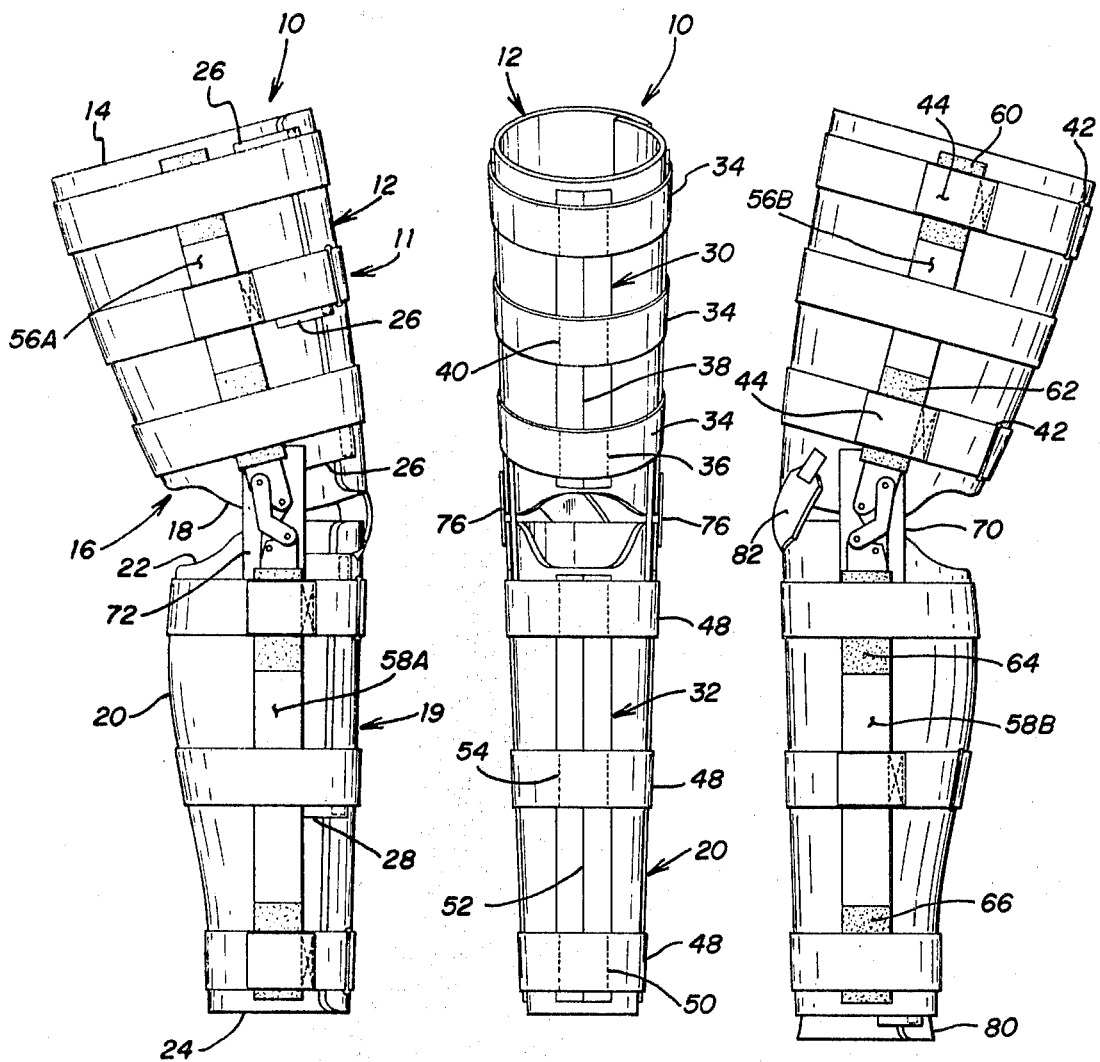
FIGS. 4 and 5 are top and bottom end views of the apparatus as it would appear when installed.

In brief, the invention includes a light-weight brace adapted to be affixed externally of a patient's leg so that it lies partly above and partly below the person's knee. The apparatus includes first and second flexible sheets of cushioned material which are adapted to be snugly wrapped around the thigh and calf. The width of each of the flexible sheets is sufficient to circumferentially envelope at least most, and preferably all, of its associated leg member. And the length of each sheet is sufficient to encompass at least half of the length of the respective leg member, so that there will be adequate leverage applied to the braces if and when the wearer moves his leg. A preferred cushioning material is a sheet of polyurethane foam (about 9 mm thick) bonded to a sheet of pile-type material having sufficient "nap" to serve as an anchor for resilient hooks of the Velcro type. Also provided are first and second pairs of elongated braces, which braces are relatively stiff so as to resist both torsion and bending loads. The first pair of elongated braces is adapted to lie on opposite sides of the wearer's thigh, and the second pair is adapted to lie on opposite sides of the wearer's calf. The elongated braces consist of structural cores which are preferably enclosed in non-metallic sheaths of vinyl or the like; the cores are bonded to said sheaths in order to inhibit any relative motion between the exterior sheaths and the interior cores. Permanently attached to the outer surface of the sheaths are pads of resilient hook material, such that the elongated braces may be selectively positioned next to and engaged with the pile side of the flexible sheets. Exact positioning of the elongated braces is a matter of choice, and a hinge which connects respective ones of the elongated braces is positioned in accordance with well-known medical principles. A plurality of non-elastic straps are provided for wrapping circumferentially around the respective leg members so as to tightly hold the respective sheet members about the thigh and calf. Additional Velcro-type fastening elements are mounted on the interior surface of the non-elastic straps and the exterior surface of the elongated braces, such that the braces may be more effectively anchored to the leg.

Referring initially to FIG. 1, an apparatus 10 for controlling the degree of motion which is permitted by one of a person's knees is shown in its completely assembled condition. The apparatus 10 includes a thigh piece 11 having a first flexible sheet 12 of cushioned material which is adapted for being wrapped snugly around the wearer's thigh. A preferred flexible material is a medium-density, open-cell polyurethane foam having a thickness of about ⅜". The preferred material is sufficiently porous to prevent sweating under normal conditions, it is light-weight, it will not usually cause an allergic skin reaction, it is readily contourable to match a person's leg, and it is capable of being washed (as required) without losing its shape or structural integrity. The length of the flexible sheet 12 will normally be sufficient to encompass more than half of the length of the wearer's thigh, in order to provide a substantial "anchor" that will insure that there will be essentially no movement of the knee—if that should be a desire of the orthopedic surgeon who is controlling treatment for an injury. A preferred length is about 30 cm. The top edge 14 of the flexible sheet 12 will normally be straight, while the bottom edge 16 will normally have a bell-shaped recess 18 in its center in order to preclude interference with the back of the leg or anchor part of the apparatus 10 when the leg is bent.

Bonded to the outer surface of the flexible sheet 12 is a polyester pile which is adapted to serve as the medium for engaging resilient hooks of the type commonly employed in fasteners of the Velcro type. By using a bonded pile/foam material for the thigh piece 11, it is possible to manufacture only one size of sheet 12 which is big enough to wrap circumferentially around essentially all adult legs. The soft material can be easily cut with scissors, however, if a small child should need to wear the apparatus 10 and there seems to be an excess of material in the sheet 12. There are no fasteners on one edge of the sheet 12, so trimming away any excess material from that edge poses no problem with regard to subsequently wrapping it around the thigh. Also, the flexible sheet 12 has a generally trapezoidal shape, so as to foster a natural fit around a person's naturally tapered thigh. The sheet 12 is preferably sized for adults with a top edge 14 of about 70 cm and a bottom edge of about 55 cm.

A second flexible sheet 20 of cushioned material, similar to the first sheet 12, is provided for snugly wrapping around the wearer's calf. And, as with the first sheet 12, the second sheet has a length which is sufficient to encompass more than half of the length of the calf—and preferably all of it. A "universally sized" calf piece 19 has a sheet 20 which is about 40 cm long. The sheet 20 also has a width which is sufficient to circumferentially envelope at least most, and preferably all, of the calf. An exemplary width for the calf piece is about 50 cm at its top edge 22 and somewhat less (e.g., about 35 cm) at its bottom edge 24. The shape of the edges 22, 24 of the lower sheet 20 may be described as almost mirror images of the edges 14, 16 on the upper piece 12, in that the upper edge 22 will typically have a bell-shaped recess in its center and the bottom edge 24 is typically straight.

On both the first and second pieces 11, 19 there are provided at one edge of the pieces a plurality of short "tabs" 26, 28 of hook-type fastener material. These tabs 26, 28, typically three in number, are utilized to initially position a respective piece 11, 19 around the wearer's leg members. That is, the tabs 26, 28 are utilized to temporarily hold a sheet in position while other connecting and fastening means are engaged. Because the tabs 26, 28 are not intended to resist the significant loads which may eventually be placed on the apparatus 10, those tabs may be made relatively small—which helps to conserve material and thereby minimizes costs.

Referring next to FIG. 2, this rear view of the apparatus 10 shows a permanently affixed stay pocket 30 in the upper piece 11 and a similar stay pocket 32 in the lower piece 19. These stay pockets 30, 32 are typically made of a vinyl material which can be easily cleaned, if necessary, and are preferably sewn directly to the pile side of the pile/foam sheet. Because the back of the thigh is generally cylindrical, the ability of the thigh piece 11 to conform closely to the thigh is improved if the rigid stays which fit into said stay pocket 30 are not too wide. In fact, a width of about 2 cm is probably about as much as would be desirable for any given stay. But, while narrow stays are desirable to improve conformity (in a circumferential direction) of the piece 11 with the thigh, it is advantageous to have significant structural support (in a longitudinal direction) at the rear of the thigh section. This desirable longitudinal support is accomplished by providing two side-by-side stays which are permanently affixed to the sheet 12 in a pocket near the center of the piece 11, with a seam down the middle of the pocket 30 being provided in order to keep the two metal stays segregated. Also secured to the thigh piece 11 with the same seams that attach the stay pocket 30 to said thigh piece are a plurality of non-elastic straps 34 which constitute the major binding elements that firmly secure the thigh piece to the wearer's thigh; these straps also lock the external braces (to be described) to the wearer's leg. There are three such flexible but non-elastic straps 34 shown in FIGS. 1-3, at least two of which (i.e., the top and bottom straps) might be considered to be mandatory, with the third (middle) strap being optional. For an adult-sized apparatus 10, it is definitely preferred that three spaced straps 34 be utilized on each of the pieces 11, 19.

Unlike the relatively soft and flexible sheets 12, 20 which have at least a certain amount of inherent resiliency, the straps 34 are not stretchable, as that term is normally used. That is, there is no predictable or desirable elasticity in the straps. A preferred strapping material is a 2" (5 cm) wide strap of non-stretch polyester having an outer surface of cut pile which is bonded to a core of $\frac{1}{8}$" open-cell, high-density polyurethane foam. The 5 cm width for a preferred strap 34 provides a means of distributing loads onto a leg member over an area that is sufficiently large as to minimize discomfort to the wearer. As for strength of the strapping, a breaking strength of over 400 pounds is preferred, in order that there will be no risk of a failure which might be occasioned by the unusual flexing of any muscle or an unexpected load caused by an accidental fall, etc. A suitable strapping material available from The Ouimet Corporation of Nashville, Tenn. is a 3-piece laminated (bonded) strap identifiable as a No. 2100 polyester pile/$\frac{1}{8}$" polyurethane foam/No. 2100 polyester pile strap.

By virtue of the fact that each strap 34 is secured to its associated thigh piece by the seams 36, 38, 40 near the centers of the straps, there are two ends which are "free" and capable of being wrapped around the thigh piece at an appropriate time. At one of the free ends of a given strap 34 is secured a D-ring 42, and the opposite end of the strap has a piece 44 of Velcro-type resilient hook material. Rolls of suitable hook material are commercially available from the Ouimet Stay & Leather Co. of Brockton, Mass. The hook-end 44 is adapted to be passed through an associated D-ring 42 and then pulled backward in order to create tension in the strap 34—prior to engaging the hooks with the outer napped (pile) surface of the strap 34. And, as indicated by FIGS. 1 and 3, it is preferable to have the plurality of straps 34 alternate in "direction", such that the top and bottom D-rings are on ends which extend in one direction from their anchoring points and the middle strap (and its associated D-ring) extends in the opposite direction. By alternating the direction of pulling on the straps in order to tighten them when installing the apparatus 10, any tendency to unreasonably twist the thigh section 11 about the underlying limb is reduced.

Also shown in FIGS. 1-3 is the calf section 19 whose general shape is defined by the flexible sheet 20, which is generally trapezoidal when layed flat and frustoconical when installed. And, as with the thigh section 11, there are a plurality of non-elastic straps 48, each of which is sewn to the back of the calf section so as to form a permanent connection therewith—in order to avoid accidental loss of the straps and to insure that they will not tend to slip down or creep up during normal leg movement. That is, the seams 50, 52, 54 which establish the stay pocket 32 in the center of the piece 19 are advantageously used to also secure straps 48 to the sheet 20. As with the above-described thigh section 11, there are D-rings and pads of Velcro hooks which are attached to respective ends of the straps 48.

Also shown in FIGS. 1 and 3 in their typical installed positions are first and second pairs of elongated braces 56, 58. Each of the braces (identified in the drawing as 56A, 56B and 58A, 58B) is relatively stiff so as to resist both torsion and bending loads. A preferred structural material for the core of the braces 56, 58 is an elongated piece of 6061 aluminum having a width of about 2 cm and a thickness of about 3 mm. A hinge (to be described) connects two adjacent ends of the structural parts or cores of the braces 56, 58, so that the length of a given brace (as measured from one distal end to the other distal end) is approximately the same as the length of two longitudinally aligned structural cores. Depending upon the height of the patient who is to wear the apparatus 10, the length of two end-to-end braces 56, 58 will typically be sized from about 56 cm in length (for a small person) to about 76 cm in length (for a relatively tall person). Rigidly secured to the structural core of each brace 56, 58 is an envelope or sheath having an interiorly facing surface with a substantial quantity of Velcro-type hook material protruding therefrom; the resilient hooks are provided so that a brace may be secured to the outer pile surface of the sections 11, 19 at essentially any desirable location. That is, the cut pile outer surfaces of the sheets 12, 20 are preferably continuous, and the sheets can be wrapped around essentially any sized leg and still provide a base for subsequently receiving a hook-type pad. Therefore, the circumference of a given person's lower limbs does not require any special handling; and a section 11, 19 of a single size can be considered to be essentially "universal" in that it will fit most if not all anticipated patients. And, regardless of how the sheets 12, 20 are wrapped around their associated limb members, there will be a napped surface available so that the hooks on braces 56, 58 can be easily affixed thereto. Of course, the determining factor for positioning a given brace 56, 58 is that the hinge members must be properly placed (in a medical sense) adjacent the wearer's knee. The proper location of such a hinge is described in an article by Dr. Augusto Sarmiento entitled "Fracture Bracing" which appeared in the July-August, 1974 issue of *Clinical Orthopedics*. Another informative article describing the proper placement and use of knee braces is an article by Dr. Vert Mooney, et al entitled "Cast-Brace Treatment for Fractures of the Distal Part of the Femur" which appeared in the December, 1970 issue of *The Journal of Bone and Joint Surgery*.

In addition to the internally facing Velcro-type resilient hooks, there are pads of externally facing hooks associated with each section of the elongated braces 56, 58. These externally facing pads 60, 62, 64, 66 are permanently bonded to the braces 56, 58 at locations where they will be engaged by the non-stretching straps 34, 48 associated with the respective sections 11, 19. A suitable bonding technique utilizes a vinyl pocket or sheath to which the aluminum cores are bonded with an agent such as a contact adhesive—of the type offered by several manufacturers such as the 3M Company under their trademark No. 8020 Modified Contact Adhesive. The respective Velcro pads are then sewn to the exterior surfaces of the vinyl pockets, thereby creating an attractive brace with adequately anchored hook pads. That is, the non-metallic pockets conceal from sight what might be considered to be strong but unsightly metallic cores; and the excellent bonding agent renders the connection between the metallic cores and the external pads of hooks essentially rigid.

Also provided for association with the elongated braces 56, 58 (as an optional "comfort" item) are narrow pieces 70, 72 of pile/foam material which are oriented so that the foam will face the wearer's knee and lie immediately under the hinge members—to preclude the metallic hinge members from coming into contact with a person's skin and causing any possible discomfort.

As mentioned briefly above, a hinge means is provided between the two structural pieces of the braces 56, 58 in order to control the angle that is formed by the brace members. There are several such hinge devices 76 that are commercially available, including both simple hinges and polycentric hinges. At one time it was widely held that simple hinges were quite adequate for bracing a knee and providing appropriate control for a person's leg members during healing. More recently, the trend has been to insist upon polycentric hinges—which more nearly approximate the exact motion of the human knee. The hinge means, per se, is not a critical part of the invention claimed in this particular application, and essentially any desired hinge may be profitably used with the construction which as previously been described.

Figure 5:
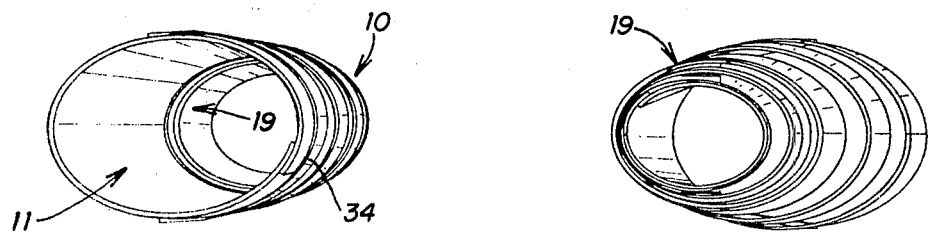
Figure 6:
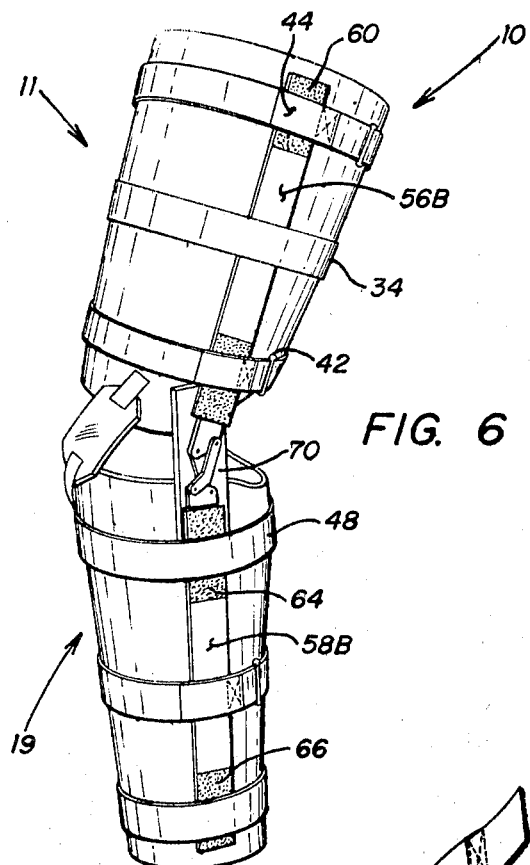
FIG. 6 is a perspective view of the apparatus.
Figure 7:
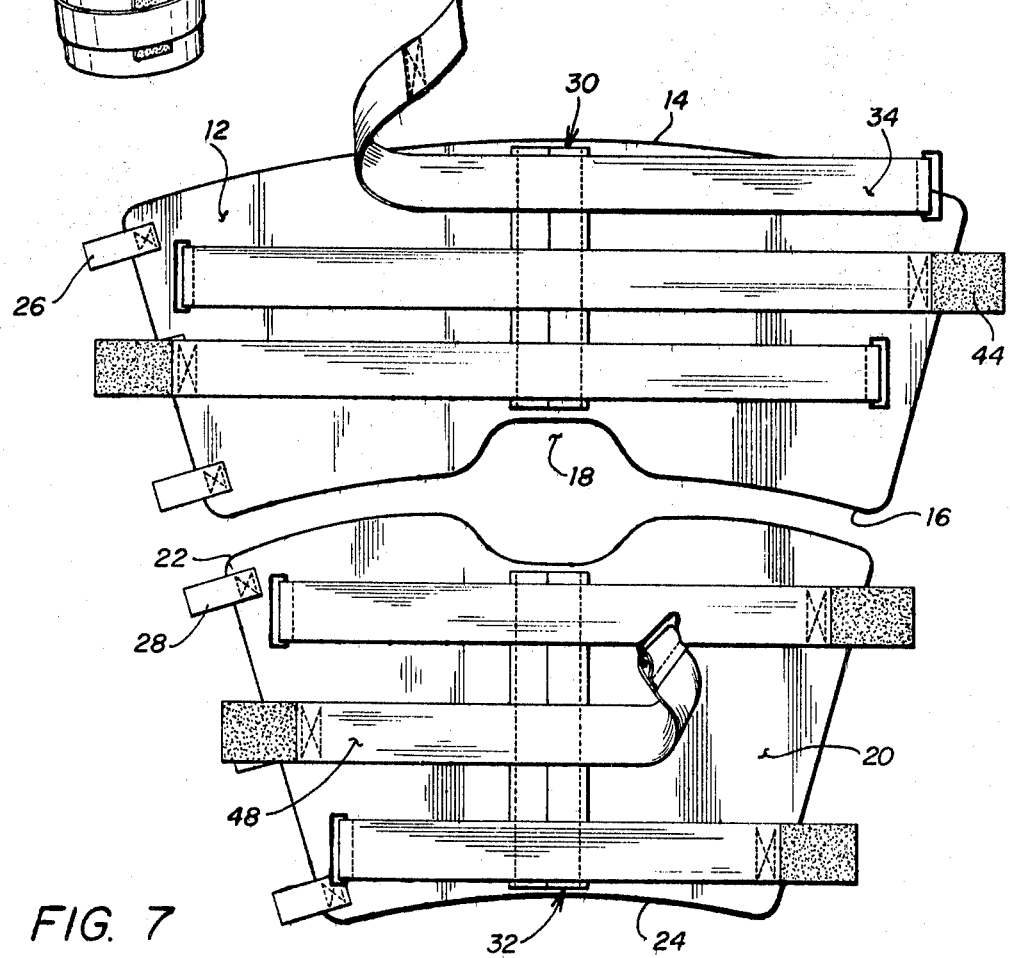
FIG. 7 is a plan view of the cushioned sheets before they are wrapped around a person's leg.

Referring next to FIGS. 4 and 5, it will be apparent that the apparatus 10 is of a generally frustoconical shape, just as a typical person's leg may be described as frustoconical. Hence, there always exists at least some possibility that the apparatus 10 as thus far described might slide downward with respect to a person's leg during active use. While tension in the straps 34, 38 will naturally tend to preclude such downward motion, it would be counterproductive to tighten those straps to the extent that circulation within the limb is cut off. As one way of inhibiting the downward "slide" of the leg sections 11, 19, an ankle cuff 80 is advantageously placed around the wearer's ankle prior to installation of the calf section 19. Such a cuff 80 ideally consists of foam/pile combination similar to the material used in sections 11, 19; and a Velcro-type hook tab is secured to one end of the strap so that it will permit a single-sized strap to be affixed to most any person's ankle. By initially installing the ankle cuff 80 on the wearer's ankle, a slightly bulbous but comfortable object is provided at the bottom of the apparatus 10, so that downward movement of the apparatus will be restricted. A small pad of Velcro hooks may advantageously be sewn to the bottom of the calf section 19, where it may engage the outer nap on the cuff 80—as one way of further inhibiting any downward movement of the apparatus. And, of course, the entire leg sections 11, 19 are removable at will and replaceable with a new, tighter "fit" around a person's leg members if, for example, some leg swelling should decrease and the apparatus begins to feel "loose". Unlike previously used plaster casts, this apparatus 10 is easily and quickly adjustable to fit a person's leg as the leg heals. Even if the leg and/or knee never really changes size during treatment, the sheets 12, 20 may be temporarily removed for washing in order to foster cleanliness of both the sheets and the patient's skin.

In use, the apparatus 10 is applied to a patient's leg by first wrapping the ankle cuff 80 securely around the ankle. Next, the calf section 19 is positioned with the center of the sheet 20 along the back of the calf, being sure to provide sufficient clearance between the bell-shaped cut-out and the back of the knee, so as to prevent contact when the knee is flexed. The calf piece 19 is held in the desired position by forcing the tabs 28 into the napped surface of the sheet 20. The thigh section 11 is installed in a like manner, with the central brace (in pocket 30) running longitudinally with the thigh along the back thereof, etc. A patella cover 82 may be optionally affixed to the two pieces 11, 19 at this time. The elongated braces 56, 58 are then attached to the sheets 12, 40 after appropriate bending has been accomplished—if necessary—to foster conformation to the patient's leg. Both ends of each of the straps are then brought forward and are tightened by pulling them to the front. While maintaining tension in the straps 34, 48 they are engaged with the outwardly facing hooks 60, 62, 64, 66. The ends with Velcro hooks are then passed through the D-rings, and the straps are tightened again before the Velcro hooks are engaged with their respective straps. The time to achieve a typical installation is usually 5 minutes or less, which contrasts very favorably with the 30 minutes or more which are required to install traditional cast braces. And the weight of the semi-rigid apparatus 10 is almost as favorable in comparison with cast braces; the weight of this apparatus ranges from 1 to 1.5 Kg, while most cast braces usually weigh more than 3 Kg. But, while the apparatus offers many functional advantages, it does not do so at the sacrifice of economy. In fact, the apparatus 10 will usually be so economical that it can be discarded after use by a single patient—while still saving the patient (or his insurance company) significant medical expenses.

While only certain preferred embodiments of the invention have been disclosed in detail herein, it will apparent to those skilled in the art that modifications thereof can be made without departing from the spirit of the invention. Thus, any specific structure shown herein is intended to be exemplary and is not meant to be limiting, except as described in the claims appended hereto.

What is claimed is:

1. An external bracing apparatus for controlling the degree of motion which is permitted to a person's knee, comprising:
  (a) first and second flexible sheets of cushioned material, one of which is adapted for snugly wrapping around the wearer's thigh and the other being adapted for snugly wrapping around the wearer's calf, and the width of each sheet being sufficient to circumferentially envelope at least most of its associated leg member, and the length of each sheet being sufficient to encompass more than half of the length of the respective leg member, and said flexible sheets being selectively removable and replaceable around the wearer's leg members;
  (b) first and second pairs of elongated braces which are adapted to be connected by hinge means, each of the braces being relatively stiff so as to resist both torsion and bending loads, and the first pair of elongated braces being adapted to lie on opposite sides of the wearer's thigh and the second pair of elongated braces being adapted to lie on opposite sides of the wearer's calf;

(c) attachment means carried by said first and second pairs of braces for adjustably positioning and selectively attaching the first and second pairs of elongated braces to attachment means the exterior sides of respective ones of the first and second flexible sheets after said sheets have been wrapped around their associated leg members;

(d) hinge means attached to respective ends of the braces which are adapted to lie on each side of the wearer's leg, and said hinge means being effective for controlling the angle that is formed by the two braces on a given side of the wearer's leg; and (e) a plurality of non-elastic straps which are selectively attachable to the outside surface of said braces and which are adapted to be wrapped circumferentially around the wearer's leg members, and said straps having connecting means so that they may be placed in tension around the wearer's leg and secured to the elongated braces.

2. The external bracing apparatus as claimed in claim 1 wherein at least a major portion of the exterior surface of the first and second flexible sheets consists a soft pile-type material which is capable of being engaged and held by a plurality of resilient hooks, and wherein a substantial portion of the inside of the surfaces of the pairs of elongated braces have affixed thereto pads of resilient hooks, such that the elongated braces may be selectively positioned at essentially any appropriate place on the sides of the flexible sheets by engaging the resilient hooks with the sheets after said sheets are wrapped around a respective leg member, and wherein the connecting means associated with the non-elastic straps constitutes a soft pile-type material fixed to the interiorly facing surfaces of the straps, and there being pads of exteriorly facing resilient hooks permanently affixed to the elongated braces, whereby the straps are adapted to be secured to the elongated braces by manually forcing together the confronting resilient hooks and pile-type material.

3. The external bracing apparatus as claimed in claim 1 wherein each of the elongated braces consist of a structural core enveloped in a non-metallic protective sheath, and the structural cores being permanently bonded to their associated sheaths, whereby the structural cores may be held in a supportive position adjacent the leg members by virtue of securely holding their associated sheaths.

4. The external bracing apparatus as claimed in claim 1 wherein the plurality of non-elastic straps are permanently anchored to their respective flexible sheets near a mid-point of said straps, whereby each strap has an interior connection to its sheet and has two free ends which are selectively engageable to hold the sheet around its leg member.

5. The external bracing apparatus as claimed in claim 1 and further including a plurality of temporary positioning tabs made of resilient hook material affixed to a side edge of each of the flexible sheets, and said tabs being selectively engageable with the exterior surface of their associated sheets, and said tabs being effective a hold a respective sheet in place around an associated leg member while the elongated braces and non-elastic straps are being manually positioned at proper places in order to complete the installation of the apparatus on the wearer's leg.

6. The method of affixing an external brace to a person in order to affect the degree of motion which can be permitted to a person's knee, comprising:

(a) initially wrapping first and second flexible sheets of cushioned material around the wearer's leg members, with one of the flexible sheets circumferentially enveloping most of the wearer's calf and the second flexible sheet circumferentially enveloping most of the wearer's thigh, and securing said first and second sheets so that they are held in place around their respective leg members;

(b) subsequently positioning and then selectively attaching first and second pairs of elongated braces to the exterior sides of respective ones of the first and second flexible sheets after said sheets have been wrapped around their associated leg members, and the two braces on a given side of the wearer's leg members being respectively connected with a hinge which is adapted for affecting the degree of motion that is realizable by a wearer's knee, and the positioning of said elongated braces being such as to properly locate the two hinges with respect to the wearer's knee; and (c) wrapping a plurality of non-elastic straps circumferentially around the flexible sheets on the wearer's leg members, and placing the straps in tension so as to closely envelop the respective flexible sheets and their associated elongated braces, and attaching said tensioned straps to the outside surface of the elongated braces, whereby the elongated braces are secured against unwanted movement by being attached to their inside surfaces to the flexible sheets and attached on their outside surfaces to the non-elastic straps.

7. The method of affixing an external brace to a person as claimed in claim 6 wherein each of the flexible sheets has an exterior pile surface and at least one tab of resilient hook material affixed to a side edge thereof, and wherein the flexible sheets are initially secured around their respective leg members by wrapping the sheets in such a way that the tabs of resilient hook material remain exposed, and then pressing said exposed tabs against the exterior pile surfaces in order to cause the hooks to engage the pile surfaces, whereby the flexible sheets may conform to the shape of essentially any leg member and be easily held in place therearound.

8. The method of affixing an external brace to a person as claimed in claim 6 and including the further step of initially applying an ankle cuff of cushioned material around the wearer's ankle before the lower flexible sheet is wrapped around the wearer's calf, whereby any tendency of the lower flexible sheet to slide downward during walking is inhibited by the presence of the ankle cuff.

* * * * *

UNITED STATES PATENT AND TRADEMARK OFFICE
CERTIFICATE OF CORRECTION

PATENT NO. : 4,407,276

DATED : October 4, 1983

INVENTOR(S) : Gary R. Bledsoe

It is certified that error appears in the above—identified patent and that said Letters Patent is hereby corrected as shown below:

Column 3, line 58, "1/8" should read --3/8--.

Column 4, line 1, "for" should read --of--; line 6, "anchor" should read --another--.

Column 7, line 35, "as" should read --has--; line 43, the numeral "38" should read --48--.

Column 8, line 20, the numeral "40" should read --20--;

Column 9, line 7, insert the word --on-- after "means"; line 25, "a" should read --of--.

Column 10, line 1, "a" should read --to--; line 39, "to", first occurrence, should read --on--.

Signed and Sealed this

Third Day of April 1984

[SEAL]

Attest:

Attesting Officer

GERALD J. MOSSINGHOFF

Commissioner of Patents and Trademarks